US010806669B2

(12) United States Patent
Yoda (10) Patent No.: US 10,806,669 B2
(45) Date of Patent: Oct. 20, 2020

(54) MEDICAL BAG

(71) Applicant: TERUMO KABUSHIKI KAISHA, Tokyo (JP)

(72) Inventor: Erika Yoda, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/710,964

(22) Filed: Sep. 21, 2017

(65) Prior Publication Data

US 2018/0008514 A1    Jan. 11, 2018

Related U.S. Application Data

(63) Continuation of application No. PCT/JP2016/059410, filed on Mar. 24, 2016.

(30) Foreign Application Priority Data

Mar. 25, 2015  (JP) .................. 2015-062070

(51) Int. Cl.
| | | |
|---|---|---|
| *A61J 1/20* | (2006.01) | |
| *A61J 1/05* | (2006.01) | |
| *A61J 1/14* | (2006.01) | |
| *A61J 1/10* | (2006.01) | |
| *A61M 1/28* | (2006.01) | |

(52) U.S. Cl.
CPC .............. *A61J 1/2093* (2013.01); *A61J 1/05* (2013.01); *A61J 1/10* (2013.01); *A61J 1/1462* (2013.01); *A61J 1/1468* (2015.05); *A61J 1/1475* (2013.01); *A61J 1/2024* (2015.05); *A61M 1/287* (2013.01)

(58) Field of Classification Search
CPC ...... A61J 1/2093; A61J 1/1468; A61J 1/2024; A61J 1/05; A61J 1/10; B29C 65/18; B29C 65/20; B29C 65/22; B29C 65/24
See application file for complete search history.

(56) References Cited

U.S. PATENT DOCUMENTS

| | | | |
|---|---|---|---|
| 4,496,046 A | 1/1985 | Stone et al. | |
| 6,364,864 B1 * | 4/2002 | Mohiuddin | ............... A61J 1/10 206/219 |

(Continued)

FOREIGN PATENT DOCUMENTS

| | | |
|---|---|---|
| EP | 1 070 495 A2 | 1/2001 |
| JP | 61-500055 A | 1/1986 |

(Continued)

OTHER PUBLICATIONS

Translation of WO 2013172235.*

(Continued)

*Primary Examiner* — Tatyana Zalukaeva
*Assistant Examiner* — Jessica R Arble
(74) *Attorney, Agent, or Firm* — Foley & Lardner LLP (57) ABSTRACT

A medical bag comprising: a bag main body comprising a flexible sheet material having an interior portion partitioned via a partition part into a first space and a second space that is smaller than the first space, a first liquid housed in the first space, and a second liquid housed in the second space. When the volume of the first liquid is set as L1 and the volume of the second liquid is set as L2, L1/L2 is 2.0 to 6.0. The partition part has a breaking strength of 5 to 25 kPa.

19 Claims, 3 Drawing Sheets

(56) References Cited

U.S. PATENT DOCUMENTS

| | | | |
|---|---|---|---|
| 2006/0172954 A1* | 8/2006 | Jensen | A61J 1/10 514/23 |
| 2007/0114144 A1 | 5/2007 | Suzuki et al. | |
| 2008/0017543 A1* | 1/2008 | Pahlberg | A61J 1/2093 206/532 |
| 2008/0176016 A1 | 7/2008 | Tateishi | |
| 2008/0255535 A1* | 10/2008 | Yoshikawa | A61J 1/2093 604/410 |
| 2010/0069817 A1* | 3/2010 | Falkvall | B01F 5/10 604/6.11 |
| 2010/0198185 A1* | 8/2010 | Gorisch | A61J 1/2093 604/410 |

FOREIGN PATENT DOCUMENTS

| | | | | |
|---|---|---|---|---|
| JP | H10-192365 A | | 7/1998 | |
| JP | 2004-208883 | | 7/2004 | |
| JP | 2005-028041 A | | 2/2005 | |
| JP | 2012-105716 A | | 6/2012 | |
| WO | WO2009/082132 | | 7/2009 | |
| WO | WO-2013172235 A1 | * | 11/2013 | A61J 1/10 |
| WO | WO2014/083612 | | 6/2014 | |

OTHER PUBLICATIONS

International Search Report and Written Opinion, PCT/JP2016/059410, Terumo Kabushiki Kaisha, 6 pages (Jun. 21, 2016).
Extended European Search Report re Application No. 16768884.5; 9 pages.
Summon to Attend Oral Proceedings dated Dec. 12, 2019 for corresponding European Patent Application No. 16768884.5.

* cited by examiner

MEDICAL BAG

CROSS-REFERENCE TO RELATED APPLICATIONS

The present application is a bypass continuation of PCT ApplicationNo. PCT/JP2016/059410, filed on Mar. 24, 2016, which claims priority to Japanese Application No. 2015-062070, filed on Mar. 25, 2015. The contents of these applications are hereby incorporated by reference in their entireties.

BACKGROUND

The present disclosure relates to a medical bag.

In a medical bag having a bag main body having an interior portion in which a liquid such as an infusion, a peritoneal dialysate, or a liquid nutrient is enclosed, in a case in which a mixture of two or more kinds of components is used during infusion, peritoneal dialysis, administration of a nutrient or the like to a patient, if the components are mixed first and then stored in the bag main body, the mixture is sometimes denaturated or deteriorated over time.

Therefore, a medical bag having a bag main body constituted by a sheet material made of a resin in which a partition part has been formed by melt-bonding the middle of the bag main body into a band-like shape, wherein the inside of the bag main body is partitioned into two spaces by this partition part, two kinds of liquids are separately housed in the respective spaces, and the medical bag is used by peeling the partition part to thereby mix the liquids in the two spaces at the time of use (a multi-chamber container) has been developed (for example, see Japanese Patent Publication No. 2004-208883). In this way, the denaturation and deterioration of a liquid such as an infusion, a peritoneal dialysate or a liquid nutrient over time can be inhibited, and the pH of the liquid can be adjusted at the time of use by peeling the partition part thereby mixing the liquids in the two spaces.

However, in a conventional medical bag, during the production of the medical bag, if sterilization is conducted at a relatively high temperature so as to improve safeness during the production of the medical bag, the partition part is strongly melt-bonded by the heat during the sterilization, and thus it may become difficult to peel the partition part at the time of use.

SUMMARY

One object of certain embodiments described herein is a medical bag having a partition part that inhibits involuntary peeling and can be easily peeled at the time of use.

In one embodiment, a medical bag includes a bag main body constituted by a flexible sheet material having an interior portion partitioned via a partition part into a first space and a second space that is smaller than the first space, a first liquid housed in the first space, and a second liquid housed in the second space. Said medical has been sterilized at 118 to 125° C. for 20 to 45 minutes. When the volume of the first liquid is set as L1 and the volume of the second liquid is set as L2, L1/L2 is 2.0 to 6.0. The partition part has a breaking strength of 5 to 25 kPa.

In one aspect, the partition part has been formed by sandwiching and melt-bonding the sheet material between an upper mold disposed on a higher side in the vertical direction than the sheet material and having a surface temperature of 130 to 145° C., and a lower mold disposed on a lower side in the vertical direction than the sheet material and having a surface temperature being 20 to 30° C. lower than the surface temperature of the upper mold.

In one aspect, a liquid formed by mixing the first liquid and the second liquid is a peritoneal dialysate.

In one aspect, the first liquid has a pH of 4.0 to 6.0.

In one aspect, the first liquid includes icodextrin.

In one aspect, the second liquid is formulated to adjust the pH of the liquid formed by mixing the first liquid and the second liquid to 6.0 to 7.5.

In one aspect, the second liquid is a buffer.

In another embodiment, a method is provided for producing a medical bag that includes a bag main body constituted by a flexible sheet material having an interior portion partitioned via a partition part into a first space and a second space being smaller than the first space, a first liquid housed in the first space, and a second liquid housed in the second space. The method includes steps of forming the partition part in the medical bag by sandwiching and melt-bonding the sheet material between an upper mold disposed on a higher side in the vertical direction than the sheet material and having a surface temperature of 130 to 145° C., and a lower mold disposed on a lower side in the vertical direction than the sheet material and having a surface temperature being 20 to 30° C. lower than the surface temperature of the upper mold; filling the first space with the first liquid having a volume of L1, and filling the second space with the second liquid having a volume of L2 to adjust L1/L2 to 2.0 to 6.0; and sterilizing the medical bag at 118 to 125° C. for 20 to 45 minutes to adjust the breaking strength of the partition part to 5 to 25 kPa.

According to certain embodiments described herein, involuntary peeling at the partition part can be inhibited even in sterilization at a relatively high temperature, and the partition part can be easily peeled in use. In this way, even a weak-handed person can use the medical bag by peeling the partition part easily and surely.

DETAILED DESCRIPTION

Hereinafter, embodiments of the medical bag will be explained in detail with reference to the attached drawings.

Figure 1:
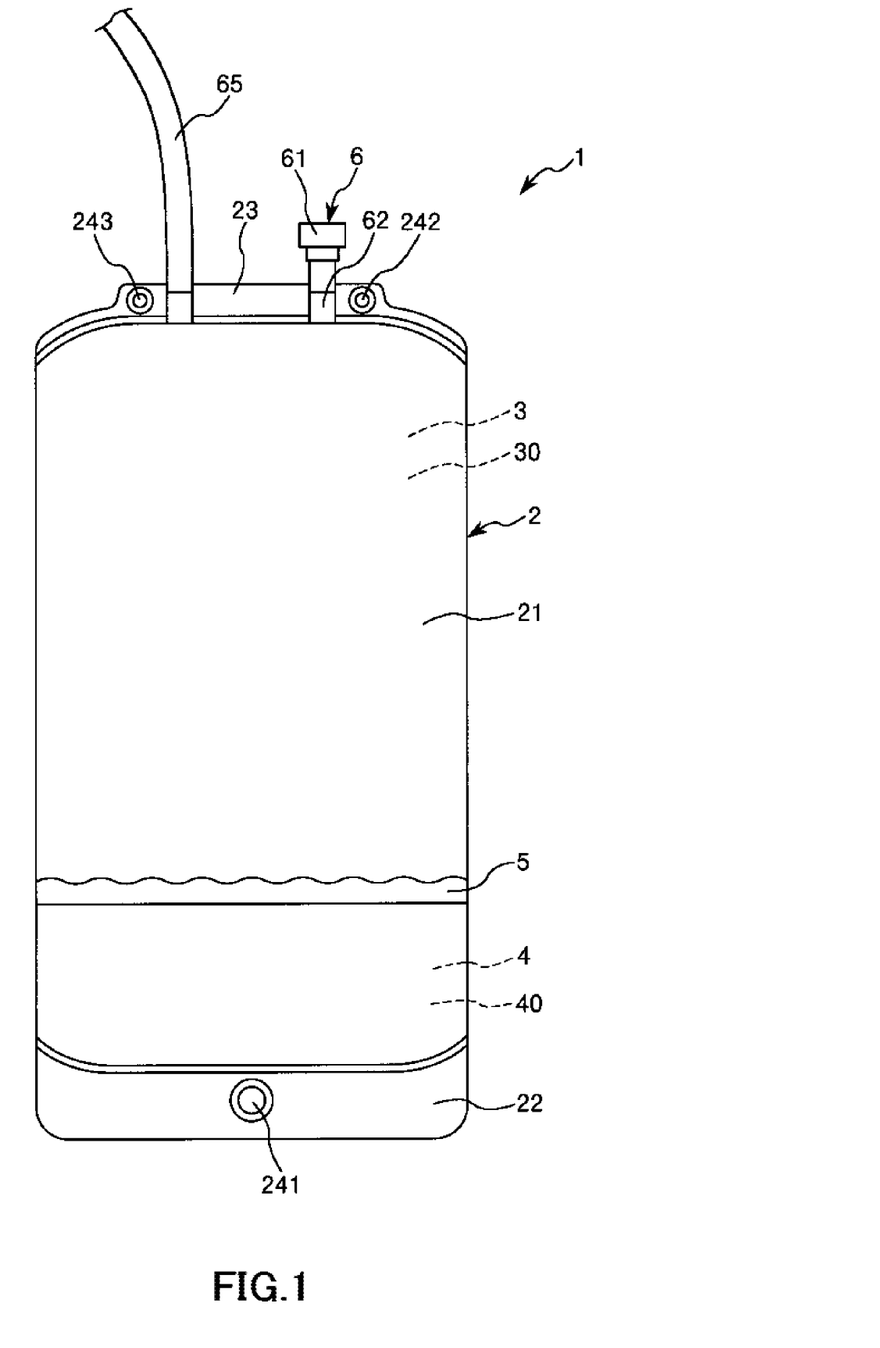
FIG. 1 is an elevational view showing an exemplary embodiment of the medical bag of the present invention.
Figure 2:
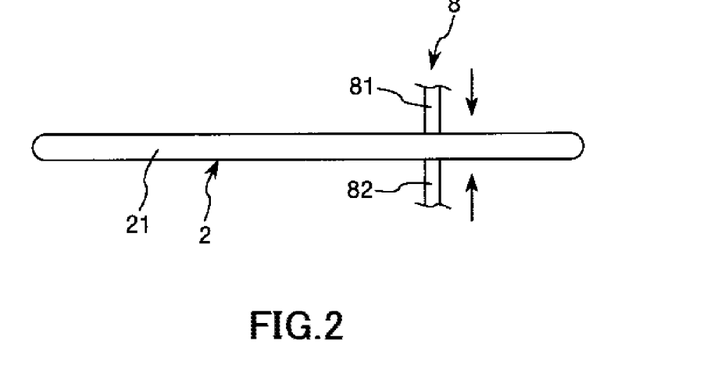
FIG. 2 is a drawing for explaining the steps for the production of the medical bag shown in FIG. 1.
Figure 3:
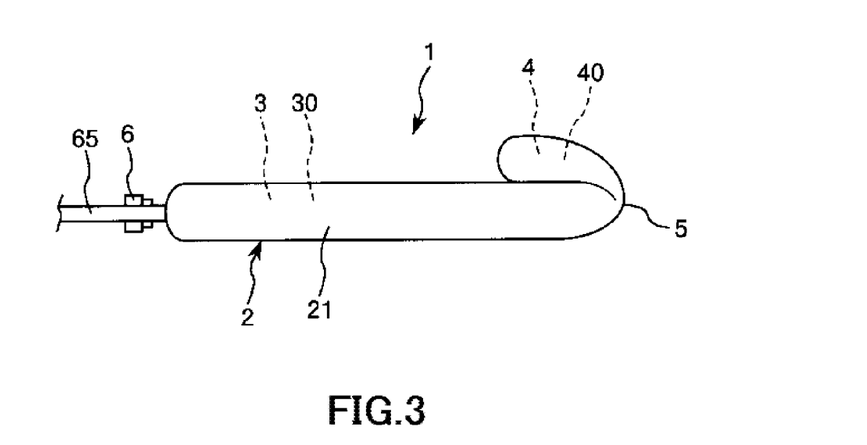
FIG. 3 is a side view showing the state that the medical bag shown in FIG. 1 is folded back at the partition part.
Figure 4:
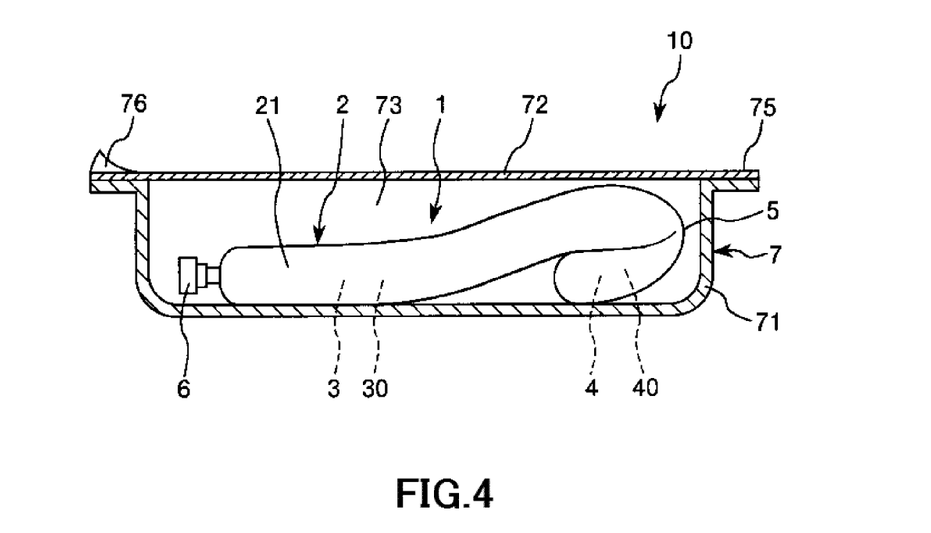
FIG. 4 is a partial cross-sectional view showing the state that the medical bag shown in FIG. 1 is housed in a packaging material.

FIG. 1 is an elevational view showing an exemplary embodiment of the medical bag. FIG. 2 is a drawing for explaining the steps for the production of the medical bag shown in FIG. 1. FIG. 3 is a side view showing a state in which the medical bag shown in FIG. 1 is folded back at the partition part. FIG. 4 is a partial cross-sectional view showing a state in which the medical bag shown in FIG. 1 is housed in a packaging material.

In the following description, for sake of convenience of explanation, the upper side in FIG. 1 is referred to as "tip", "above" or "upward", and the lower side is referred to as "base end", "below" or "downward", the right side is referred to as "right", and the left side is referred to as "left".

Furthermore, the upper side in FIGS. 2 to 4 is referred to as "above" or "upward", the lower side is referred to as "below" or "downward", the right side is referred to as "tip" or "right", and the left side is referred to as "base end" or "left".

The medical bag 1 shown in FIG. 1 is housed in a packaging material 7 in a state in which it is folded back at a partition part 5, which will be described below, and a medical bag individually-packaged body 10 is constituted by the medical bag 1 and the packaging material 7 (see FIG. 4). In the following, the state in which the medical bag 1 is folded back at the partition part 5 is also simply referred to as "folded-back state".

As shown in FIG. 1, the medical bag 1 includes a bag main body 2, an injection port 6 and a tube 65, and the bag main body 2 is filled with a liquid. This medical bag 1 is a multi-chamber container in which the interior portion of the bag main body 2 is partitioned into plural spaces, which are two spaces in this exemplary embodiment, i.e., a first space 3 and a second space 4.

The bag main body 2 is produced by using, for example, a sheet material 21 mentioned below, which is molded into a cylindrical shape by an inflation molding process or the like and formed of a flexible soft material. The sheet material 21 may be for plural bag main bodies and used by cutting into every sheet for one bag main body, or may be for one bag main body. In the following, in a case in which the sheet material 21 is for plural bag main bodies, the sheet material 21 is referred to as "sheet material 21" for either of before and after the cutting of the sheet material 21.

The bag main body 2 is formed by sealing both end parts of the sheet material 21 by melt-bonding such as heat melt-bonding or high frequency wave melt-bonding or adhesion to form a bag-like shape. The sealed part 22 at the base end side and the sealed part 23 at the tip end of the bag main body 2 have been respectively cut into desired shapes.

A pore 241, which is used for hanging the medical bag 1 on a hanger or the like, is formed on approximately the center part of the sealed part 22 at the base end side of the bag main body 2. Similarly, pores 242 and 243, which are used for hanging the medical bag 1 on a hanger or the like, are formed on the right side and left side of the sealed part 23 at the tip side of the bag main body 2.

A partition part 5 is formed in the middle in the vertical direction of the main body 2 of this bag in FIG. 1, and the interior portion of the bag main body 2 is partitioned into a first space 3 and a second space 4 by this partition part 5.

This partition part 5 is formed into a straight line in the bag main body 2. Furthermore, the partition part 5 extends in the transverse direction of the bag main body 2 in FIG. 3, and is formed so as to cross the bag main body 2.

Furthermore, a difference is provided to the width of the partition part 5 along the transverse direction in FIG. 3. That is, the lower end of the partition part 5 forms a straight line, and the upper end forms a wave shape. In this way, as mentioned below, when the partition part 5 is peeled by pressing the part of the first space 3 of the medical bag 1, among the parts of the above-mentioned wave shape of the partition part 5, the peeling proceeds from the convex part at the tip side.

Furthermore, as mentioned below, the partition part 5 is formed by melt-bonding the sheet material 21 of the bag main body 2 into a band-like shape by using a mold 8 (see FIG. 2). Furthermore, the partition part 5 is constituted by, for example, a part on the first space 3 or the second space 4 of the medical bag 1, preferably by a part that is sealed so weakly that the part is easily peeled by pressurizing the part of the first space 3 by hands to thereby increase the inner pressure of the first space 3. In this way, the blocking by the partition part 5 can be eliminated by an easy operation without using any special instrument or the like, whereby the liquid in the first space 3 and the liquid in the second space 4 can be mixed. In a case in which the partition part 5 is peeled, it is preferable to hang the medical bag 1 on a hanger or the like so that the first space 3 of the medical bag 1 is positioned on the upper side in the vertical direction and the second space 4 is positioned on the lower side in the vertical direction, and press the part of the first space 3 of the medical bag 1.

Furthermore, it is preferable that the breaking strength of the partition part 5 is 5 to 25 kPa.

The breaking strength of the partition part 5 is an internal pressure of the medical bag 1 when the medical bag 1 is hanged so that the first space 3 of the medical bag 1 is set as the upper side in the vertical direction and the second space 4 is set as the lower side in the vertical direction, a part of the first space 3 of the medical bag 1 is pressurized, and the partition part 5 is peeled.

When the breaking strength is larger than the upper limit value, if one intends to peel the partition part 5 in use, then the partition part 5 becomes difficult to be peeled.

Furthermore, if the breaking strength is lower than the lower limit value, then the partition part 5 may be involuntarily peeled.

Without limiting to a case in which the whole part of the partition part 5 is constituted by a weak sealed part, a part of the partition part 5 may be constituted by a weak sealed part.

Furthermore, the partition part 5 is positioned closer to the base end side from the center of the vertical direction of the bag main body 2 in FIG. 1, and in this way, the volume of the second space 4 is preset to be smaller than the volume of the first space 3.

Furthermore, when the volume of the first space 3 is set as V1 and the volume of the second space 4 is set as V2, V1/V2 is not specifically limited and suitably preset according to the various conditions, and when a ratio L1/L2 of the volume L1 of a first liquid 30 to the volume L2 of a second liquid 40 mentioned below is taken into consideration, V1/V2 is preferably 2.0 to 6.0, more preferably 4.0 to 6.0, further preferably 4.5 to 5.5.

When V1/V2 is higher than the upper limit value, it becomes easy to undergo a high internal pressure from the first space 3 depending on condition other than the high internal pressure, and thus the partition part 5 may be involuntarily peeled.

Furthermore, when the partition part 5 is peeled in use, the part in which the first liquid 30 is housed in the medical bag 1 is pressurized. Therefore, if V1/V2 is lower than the above-mentioned lower limit value, then it becomes difficult to undergo a high internal pressure from the first space 3 depending on other conditions, and in a case in which one intends to peel the partition part 5 in use, the partition part 5 is difficult to peel.

Furthermore, the volume V1 of the first space 3 is not specifically limited and is suitably preset depending on various conditions, and when the volume L1 of a first liquid 30 mentioned below is taken into consideration, the volume L1 is preferably 1,000 to 2,000 mL.

Furthermore, the volume V2 of the second space 4 is not specifically limited and is suitably preset depending on various conditions, and when the volume L2 of a second liquid 40 mentioned below is taken into consideration, the volume L2 is preferably 100 to 500 mL.

In the first space 3 and the second space 4, a first liquid 30 and a second liquid 40 having different compositions from each other are housed.

Until use, the first liquid 30 and the second liquid 40 are separately stored without being mixed, and at the time of use, the partition part 5 is peeled to allow the first space 3 and the second space 4 to be in communication, whereby the first liquid 30 and the second liquid 40 are mixed. In this way, the denaturation deterioration and the like of the first liquid 30 and the second liquid 40 can be inhibited, whereby an intended medicinal effect can be obtained more surely.

For example, by housing an acidic solution containing a component stable under acidic condition and a buffer that makes the acidic solution neutral (a pH adjusting agent) or an alkaline solution separately, i.e., in the first space 3 and the second space 4, respectively, the denaturation, decomposition, deterioration, coloration, discoloration, generation of a precipitated product, and the like of such liquid can be inhibited.

The liquid obtained by mixing the first liquid 30 and the second liquid 40 is not specifically limited, and examples include peritoneal dialysates, saline, electrolyte solutions, Ringer's solution, high calorie infusions, glucose solutions, injection water, oral nutrients and the like.

Specific examples of the first liquid 30 and the second liquid 40 will be explained using a case in which the liquid formed by mixing the first liquid 30 and the second liquid 40 is a peritoneal dialysate. However, the first liquid 30 and the second liquid 40 described below are only examples.

Firstly, it is preferable that peritoneal dialysate obtained by mixing the first liquid 30 and the second liquid 40 after the sterilization has a pH of 6.0 to 7.5.

Furthermore, the first liquid 30 may be a liquid having icodextrin, and more specifically, the first liquid 30 may be a liquid having icodextrin and sodium chloride.

Furthermore, it is preferable that the first liquid 30 has a pH of preferably 4.0 to 6.0, more preferably 4.5 to 5.5 in terms of a value after the sterilization.

Furthermore, the second liquid 40 may be a buffer (a pH adjusting agent), and specifically a buffer for adjusting the pH of the liquid obtained by mixing the first liquid 30 and the second liquid 40 after the sterilization to 6.0 to 7.5.

This second liquid 40 may include, for example, at least one of sodium hydroxide and sodium hydrogen carbonate.

Furthermore, it is preferable that the second liquid 40 has, for example, at least one of lactic acid, lactate and the like as an alkalinizing agent.

Examples of the lactate include sodium lactate, potassium lactate, calcium lactate and the like, and sodium lactate is preferable among these.

Furthermore, when the volume of the first liquid 30 housed is set as L1 and the volume of the second liquid 40 housed is set as L2, the ratio L1/L2 of L1 and L2 maybe 2.0 to 6.0, preferably 4.0 to 6.0, and more preferably 4.5 to 5.5.

By presetting the above-mentioned L1/L2 to be within the above-mentioned range, in a case in which the above-mentioned liquid having icodextrin is used as the first liquid 30 and the above-mentioned buffer is used as the second liquid 40, the stability of the first liquid 30, and the stability and pH of the liquid formed by mixing the first liquid 30 and the second liquid 40 can be optimized.

Furthermore, if L1/L2 is larger than the above-mentioned upper limit value, then the partition part 5 may be involuntarily peeled during transportation and storage.

Furthermore, when the partition part 5 is peeled at the time of use, the part in which the first liquid 30 having a large volume is housed is pressurized, and if L1/L2 is smaller than the above-mentioned lower limit value, then the partition part 5 becomes difficult to undergo a high internal pressure in use, and thus becomes difficult to be peeled.

Furthermore, the volume L1 of the first liquid 30 is not specifically limited and is suitably preset depending on various conditions, and is preferably 1,000 mL to 2,000 mL.

Furthermore, the volume L2 of the second liquid 40 is not specifically limited and is suitably preset depending on various conditions, and is preferably 100 mL to 500 mL.

Furthermore, predetermined display patterns such as a scale, a volume, a drug concentration, type, information for attention, a list of components and an expiration date are printed on the surfaces of predetermined positions of the bag main body 2.

Furthermore, an injection port 6 may be disposed on the right side of the tip part of the bag main body 2, and the end part of the tube 65 may be connected to the left side.

The tube 65 has a function to eject at least the mixed liquid of the first liquid 30 and the second liquid 40, and is connected to, for example, the user side. In addition, a peelable second partition part (not illustrated) such as the above-mentioned partition part 5, or the like may be disposed in the vicinity of the end part of the tube 65 of the bag main body 2 so as to partition the first space 3 into a third space (not illustrated) that is in communication with the end part of the tube 65 and a fourth space (not illustrated) that is positioned outside of the third space.

Furthermore, the injection port 6 has a function to inject a predetermined liquid such as the first liquid 30 into at least the first space 3, and includes an injection port main body 61 equipped with an elastic plug, and an outer cylinder 62 installed on the outside of the injection port main body 61.

The outer cylinder 62 is interposed between sheet materials 21 and 21 on the sealed part 23 at the tip part of the bag main body 2, and is fixed by the sealed part 23. The joining property and adhesion between the outer cylinder 62 and the sheet material 21 are high, and thus liquid spill and the like can be surely inhibited.

The above-mentioned injection port 6 may have a function of ejecting the predetermined liquid and the like, and plural injection ports may be installed.

Furthermore, the sheet material 21 may be produced by not only the above-mentioned inflation molding process, but also by various methods such as a T-die process, a blow-molding process, a dry laminate process, a hot melt laminate process, a co-extrusion inflation process, a co-extrusion T-die process and a hot press process.

Furthermore, in order to effectively inhibit the denaturation and deterioration of the first liquid 30 and the second liquid 40, the sheet material 21 is preferably a sheet material having low gas permeability as possible, i.e., having gas barrier property.

However, the gas permeability of the sheet material 21 is preset to be higher than the gas permeability of a packaging material 7, which will be mentioned below. In this way, during sterilization with high pressure steam, which will be mentioned below, the medical bag 1 in the packaging material 7 can be sterilized by utilizing water vapor of the first liquid 30 and the second liquid 40 that have permeated the bag main body 2.

As the constitutional material for the sheet material 21, it is preferable to use a resin containing a polyolefin, specifically polypropylene as a main component, because this constitutional material has heat resistance andwater resistance by which the constitutional material can withstand high pressure vapor sterilization (autoclave sterilization).

In a case in which polypropylene is used as a main component, the content ratio of the polypropylene in the constitutional material of the sheet material 21 is preferably more than 50 wt %, more preferably about 60 to 95 wt %, further preferably about 70 to 80 wt %.

Furthermore, the average molecular weight Mw of the used polypropylene is not specifically limited, and is preferably about 800,000 to 3,000,000.

Specifically, examples of the constitutional material of the sheet material 21 include only polypropylene, a copolymer of polypropylene with one kind or two or more kinds of other polymer(s), a polymer alloy of polypropylene with one kind or two or more kinds of other polymer(s), a mixture of polypropylene with one kind or two or more kinds of other polymer(s), and the like.

Examples of the above-mentioned other polymer include thermoplastic resins such as polyethylene, EVA, polyamides and polyesters, the thermoplastic elastomers mentioned below, and the like, and one kind or a combination of two or more kinds of these can be used.

Furthermore, as a preferable constitutional material for the sheet material 21, a soft resin obtained by softening by blending polypropylene with a thermoplastic elastomer such as a styrene-based, polyamide-based or a polyester-based thermoplastic elastomer can be used. As the thermoplastic elastomer, styrene-based thermoplastic elastomers such as a styrene-butadiene copolymer and a styrene-ethylene-butylene-styrene block copolymer are preferable. This is because this material has high strength and is very flexible, has high heat resistance, specifically high heat resistance during sterilization, has high water resistance, and is good in processability, and thus can be decrease the production cost.

In addition, the content rate of the thermoplastic elastomer in the constitutional material of the sheet material 21 is preferably about 0 to 49 wt %, more preferably about 10 to 40 wt %.

Next, the packaging material 7 will be explained. As shown in FIG. 4, the packaging material 7 is constituted by a pair of sheet materials, i.e., the first sheet material 71 and the second sheet material 72. The shape of a plane view of these first sheet material 71 and second sheet material 72, i.e., the shape when these sheet materials are seen from the upper side of FIG. 4, have approximately the same shape, and either of these sheet materials has an approximately square shape. In response to this, the shape of a plane view of the packaging material 7 also has an approximately square shape.

The packaging material 7 is formed by superposing the first sheet material 71 and the second sheet material 72, sealing the edge parts of these sheet materials by melt-bonding such as heat melt-bonding, high frequency wave melt-bonding or ultrasonic melt-bonding, or by adhesion by an adhesive, a solvent or the like to forma bag-like shape. The above-mentioned sealed part, i.e., the sealed part 75 has been formed into a band-like shape along the outer periphery part of the packaging material 7.

The second sheet material 72 has been formed into a plane shape. On the other hand, the first sheet material 71 has been formed into a projected shape in which the medical bag 1 can be housed. That is, the first sheet material 71 has a bulge corresponding to the shape and size of the medical bag 1 in a folded-back state. In addition, the medical bag 1 having a folded-back state is formed in the interior portion of this bulge, i.e., a space 73.

This space 73 is surrounded by the first sheet material 71, the second sheet material 72 and the sealed part 75, and is isolated from outside in an air-tight manner. Therefore, in a case in which the sheet material of the constitutional material mentioned below is used, preferable moisture proof property and sterile state are kept until use in the medical bag 1 housed in the space 73.

A peel tab 76 formed by avoiding sealing of the sheet material is provided to the end part of this packaging material 7, which is the endpartonthe left side in FIG. 2 in the illustrated constitution. By pulling, for example, the second sheet material 72 with this peel tab 76 in the direction such that the second sheet material 72 departs from the first sheet material 71, the sealed part 75 can be peeled, and thus the packaging material 7 can be opened.

Furthermore, the constitutional material of the first sheet material 71 and the constitutional material of the second sheet material 72 may be the same or different. For example, the first sheet material 71 may be constituted by a material that is harder than the material of the second sheet material 72. Furthermore, it is preferable that the second sheet material 72 is a flexible sheet material. In this way, when the first sheet material 71 departs from the second sheet material 72, the sealed part 75 can be easily peeled.

Furthermore, in order to ensure the visibility of the contents, it is preferable that at least one of the first sheet material 71 and the second sheet material 72 is transparent.

Furthermore, it is preferable that the packaging material 7 has a gas barrier property.

Thus, because the packaging material 7 has a gas barrier property in this way, entering of water vapor from the outside to the inside of the space 73 can be inhibited. Consequently, the moisture proof property in the space 73 can be kept.

As the first sheet material 71 and the second sheet material 72 that constitute the packaging material 7, i.e., the sheet materials having the above-mentioned gas barrier property, single layer films of polyolefin resins such as polyethylene and polypropylene, blend resins of these polyolefin resins, polyester resins such as polyethylene terephthalate, polyvinylidene chloride, vinyl chloride-vinylidene chloride copolymers, and the like; films obtained by depositing aluminum, silica or the like on these films; and metal foils or metal foil-containing films such as aluminum films and aluminum-laminated films can be used. Furthermore, films obtained by laminating two or more of these films can also be used.

As the method for producing the first sheet material 71 and the second sheet material 72 that constitute such packaging material 7, for example, a similar method to that described above as the method for producing the sheet material 21 can be used.

Furthermore, although a constitution in which the second sheet material 72 has been formed into a plane shape and the first sheet material 71 is packaged by a blister packaging that has been molded into a projected shape in which the medical bag 1 can be housed has been explained in this exemplary embodiment, the constitution may be such that the medical bag 1 is packaged by a laminate packaging and a film packaging or the like, or may be such that the medical bag 1 is packaged by using a molded container.

Next, the methods for producing a medical bag 1 and a medical bag individually-packaged body 10 will be explained.

Firstly, for example, a sheet material 21 that has been molded into a cylindrical shape by an inflation molding process or the like is prepared.

As mentioned above, it is preferable that this sheet material 21 is constituted by a polyolefin, specifically a resin containing polypropylene as a main component. Because the constitutional materials for the sheet material 21 have been already explained, the explanation thereof is omitted.

Furthermore, sealed parts 22 and 23 are respectively formed on the sheet material 21. In order to dispose an injection port 6 and a tube 65 later, pores (not illustrated) are formed on a part of the sealed part 23. Furthermore, a pore (not illustrated) is also formed on a part of the sealed part 22 so that the second liquid 40 may be later filled.

Next, as shown in FIG. 2, the sheet material 21 is melt-bonded by using a mold 8 to form a partition part 5.

The mold 8 has an upper mold 81 that is positioned on an upper side in the vertical direction than the sheet material 21 and a lower mold 82 that is positioned on a lower side in the vertical direction than the sheet material 21.

The upper mold 81 and the lower mold 82 are respectively constituted by, for example, various metal materials, and the surfaces thereof may be coated with a resin material such as silicon or not coated. However, it is preferable that the upper mold 81 is not coated and the lower mold 82 is coated.

The sheet material 21 is melt-bonded by sandwiching the sheet material 21 with such upper mold 81 and lower mold 82, and heating. The conditions for the melt-bonding are as follows.

The surface temperature of the upper mold 81 is 130 to 145° C., preferably 135 to 145° C.

When the surface temperature of the upper mold 81 is higher than the above-mentioned upper limit value, the sheet material 21 is excessively melt-bonded, and when one intends to peel the partition part 5 at the time of use, the partition part 5 becomes difficult to be peeled.

Furthermore, when the surface temperature of the upper mold 81 is lower than the above-mentioned lower limit value, it is possible that the melt-bonding of the sheet material 21 becomes insufficient, and the partition part 5 is involuntarily peeled.

Furthermore, the surface temperature of the lower mold 82 is preset to be lower than the surface temperature of the above-mentioned upper mold 81. In this way, a difference can be provided to the degrees of the melt-bonding between the side of the upper mold 81 and the side of the lower mold 82, i.e., the surface side and the rear side of the partition part 5, and thus the side of the upper mold 81 of the partition part 5 can further be shrunk. In a case in which the medical bag 1 is folded back at the partition part 5, the strain on the medical bag 1 can be decreased by folding back the medical bag 1 so that the surfaces at the side of the upper mold 81 of the medical bag 1 are brought into contact.

In this case, the difference between the surface temperature of the lower mold 82 and the surface temperature of the upper mold 81 is 20 to 30° C., preferably 22 to 30° C.

When the above-mentioned difference is higher than the above-mentioned upper limit value, it is possible that the melt-bonding of the sheet material 21 becomes insufficient, and thus the partition part 5 is involuntarily peeled.

Furthermore, when the above-mentioned difference is smaller than the above-mentioned lower limit value, the sheet material 21 may be excessively melt-bonded, and thus when one intends to peel the partition part 5 in use, the peeling thereof becomes difficult.

Furthermore, the melt-bonding time is not specifically limited and is suitably preset depending on various conditions, and is preferably 2.0 to 5.0 seconds, more preferably 2.0 to 4.0 seconds.

When the melt-bonding time is longer than the above-mentioned upper limit value, the sheet material 21 may be excessively melt-bonded depending on other conditions, and thus when one intends to peel the partition part 5 in use, the peeling thereof becomes difficult.

Furthermore, when the melt-bonding time is shorter than the above-mentioned lower limit value, it is possible that the sheet material 21 is insufficiently melt-bonded depending on other conditions, and thus the partition part 5 is involuntarily peeled.

Furthermore, the pressure by the mold 8 during the melt-bonding is not specifically limited and is suitably preset depending on various conditions, and is preferably 0.2 to 0.5 MPa, more preferably 0.3 to 0.4 MPa.

When the above-mentioned pressure is higher than the above-mentioned upper limit value, the sheet material 21 may be excessively melt-bonded depending on other conditions, and thus when one intends to peel the partition part 5 in use, the peeling thereof becomes difficult.

Furthermore, when the above-mentioned pressure is smaller than the above-mentioned lower limit value, it is possible that the sheet material 21 is insufficiently melt-bonded depending on other conditions, and thus the partition part 5 is involuntarily peeled.

Next, an injection port 6 and a tube 65 are respectively melt-bonded to the sheet material 21, i.e., the bag main body 2. Each melt-bonding may be conducted before forming the partition part 5.

Next, a first space 3 is filled with a first liquid 30, and a second space 4 is filled with a second liquid 40. The first space 3 is filled with a first liquid 30 through, for example, an injection port 6. Furthermore, the second space 4 is filled with the second liquid 40 by, for example, directly inserting a nozzle for liquid filling in the second space 4, and closing the second space 4 by sealing the pore from which the nozzle was inserted after the second space 4 is filled with the second liquid 40. In this way, a medical bag 1 before sterilization can be obtained.

Next, as shown in FIG. 3, the medical bag 1 is folded back at the partition part 5. In this case, the medical bag 1 is folded back so that the surfaces at the side of the upper mold 81 side are brought into contact. As mentioned above, since the part at the side of the upper mold 81 of the partition part 5 has shrunk more than the part at the side of the lower mold 82, the load on the medical bag 1 can be decreased by folding back in this way.

Furthermore, as shown in FIG. 4, the surface side and the rear side of the medical bag 1 are inverted, the medical bag 1 is housed in a packaging material 7 in a folded-back state, and the packaging material 7 is sealed. Specifically, the medical bag 1 in a folded-back state is housed in the first sheet material 71, the first sheet material 71 and the second sheet material 72 are superposed, and the edge parts thereof are sealed by melt-bonding or adhesion. It is needless to say that it is not necessary to invert the surface side and the rear side of the medical bag 1. In this way, a medical bag individually-packaged body 10 before sterilization can be obtained. In addition, by packaging the medical bag 1 in a state that the medical bag 1 is folded back at the partition part 5, the partition part 5 can be inhibited from peeling when the medical bag 1 is pressurized, for example, when the medical bag individually-packagedbody 10 is transported. Furthermore, the medical bag 1 has an advantage that the medical bag 1 takes lesser effort than that in a case in which the medical bag 1 is folded back after high pressure vapor sterilization, which will be mentioned below.

Subsequently, for the medical bag individually-packaged body 10, i.e., the medical bag 1 housed in the packaging material 7, the entirety of the packaging material 7 is subjected to sterilization such as high pressure vapor sterilization.

The conditions for the sterilization are as follows.

The temperature for the sterilization is 118 to 125° C.

In this way, the medical bag 1 can be sterilized necessarily and sufficiently, and thus the medical bag 1 having high safeness can be provided.

However, if the sterilization temperature is higher than the above-mentioned upper limit value, then the sheet material 21 may be excessively melt-bonded by the heat during the sterilization, and thus when one intends to peel the partition part 5 in use, the partition part 5 becomes difficult to be peeled.

Alternatively, if the sterilization temperature is lower than the above-mentioned lower limit value, then it is possible that the safeness of the medical bag 1 is decreased, the sheet material 21 may be melt-bonded insufficiently, and the partition part 5 may be involuntarily peeled.

Furthermore, the sterilization time is 20 to 45 minutes, preferably 30 to 40 minutes.

When the sterilization time is longer than the above-mentioned upper limit value, the sheet material 21 is excessively melt-bonded by the heat during the sterilization, and thus when one intends to peel the partition part 5 in use, the partition part 5 becomes difficult to be peeled.

Furthermore, when the sterilization time is shorter than the above-mentioned lower limit value, it is possible that the safeness of the medical bag 1 is decreased, the sheet material 21 is melt-bonded insufficiently, and the partition part 5 is involuntarily peeled.

The sterilization method is not limited to high pressure vapor sterilization, and the sterilization may be conducted by other method.

By the above-mentioned method, a medical bag individually-packaged body 10 having a medical bag 1 having a partition part 5 having a breaking strength of 5 to 25 kPa can be obtained.

As explained above, according to this medical bag 1, a medical bag that is surely sterilized and thus is safe can be provided. Furthermore, the involuntary peeling of the partition part 5 can be inhibited, and the partition part 5 can be easily peeled in use. In this way, even a weak-handed person such as an aged person or a woman can use the medical bag 1 by peeling the partition part 5 easily and surely.

EXAMPLES

Next, specific Examples will be explained.

Example 1

A medical bag was produced as follows.

A sheet material having a cylindrical shape obtained by molding polypropylene was melt-bonded by using a mold to form a partition part. The surface temperature of the upper mold was set to 130° C., and the surface temperature of the lower mold was set to 105° C.

Subsequently, a first space of the bag main body was filled with a first liquid, a second space was filled with a second liquid, and a necessary part was sealed. The ratio L1/L2 of the volume of the first liquid L1 and the volume of the second liquid L2 was set to 4.0.

Subsequently, the medical bag was housed in a packaging material and sterilized at 118° C. for 30 minutes.

Furthermore, the medical bag was hanged on a hanger so that the first space in which the first liquid was housed in the medical bag was positioned on the upper side in the vertical direction and the second space in which the second liquid was housed was positioned on the lower side in the vertical direction, a part on the first space of the medical bag was pressurized, and whether or not the partition part was peeled was confirmed (the same applied to Examples 2 and 3, and Comparative Examples 1 to 6). This test was conducted by plural persons including men and women.

In the results of the test of Example 1, all of the persons were able to peel the partition part, and thus good results were obtained. Furthermore, the average value of the internal pressures when the partition part was peeled was 8.0 kPa.

EXAMPLE 2

A medical bag was produced in a similar manner to that of Example 1, except that the surface temperature of the upper mold was changed to 140° C., the surface temperature of the lower mold was changed to 115° C., L1/L2 was changed to 5.0, and the conditions for the sterilization were changed to 121° C. and 35 minutes, relative to Example 1.

In the results of the test of Example 2, all of the persons were able to peel the partition part, and thus good results were obtained. Furthermore, the average value of the internal pressures when the partition part was peeled was 15.0 kPa.

EXAMPLE 3

A medical bag was produced in a similar manner to that of Example 1, except that the surface temperature of the upper mold was changed to 145° C., the surface temperature of the lower mold was changed to 125° C., L1/L2 was changed to 6.0, and the conditions for the sterilization were changed to 121° C. and 30 minutes in Example 1.

In the results of the test of Example 3, all of the persons were able to peel the partition part, and thus good results were obtained. Furthermore, the average value of the internal pressures when the partition part was peeled was 22.0 kPa.

COMPARATIVE EXAMPLE 1

Production of a medical bag was tried in a similar manner to that of Example 1, except that the surface temperature of the upper mold was changed to 125° C., the surface temperature of the lower mold was changed to 95° C., and L1/L2 was changed to 4.0 in Example 1. However, the partition part was peeled during the production, and thus a medical bag was not able to be produced.

COMPARATIVE EXAMPLE 2

A medical bag was produced in a similar manner to that of Example 1, except that the surface temperature of the upper mold was changed to 150° C., the surface temperature of the lower mold was changed to 120° C., L1/L2 was changed to 5.0, and the conditions for the sterilization were changed to 125° C. and 20 minutes in Example 1.

In the results of the testing of Comparative Example 2, the partition part could not be peeled.

COMPARATIVE EXAMPLE 3

A medical bag was produced in a similar manner to that of Example 1, except that the surface temperature of the upper mold was changed to 140° C., the surface temperature of the lower mold was changed to 115° C., L1/L2 was changed to 1.5, and the conditions for the sterilization were changed to 121° C. and 35 minutes in Example 1.

In the results of the test of Comparative Example 3, the men were able to peel the partition part, whereas although the women were able to peel the partition part, the operation therefor was not easy. Furthermore, the average value of the internal pressures when the partition part was peeled was 26.0 kPa.

COMPARATIVE EXAMPLE 4

A medical bag was produced in a similar manner to that of Example 1, except that the surface temperature of the upper mold was changed to 140° C., the surface temperature of the lower mold was changed to 115° C., L1/L2 was changed to 6.5, and the conditions for the sterilization were changed to 121° C. and 35 minutes in Example 1.

In the results of the test of Comparative Example 4, all of the persons were able to peel the partition part. Furthermore, the average value of the internal pressures when the partition part was peeled was 12.0 kPa.

However, when impact resistance tests were conducted on plural samples of Comparative Example 4, the partition part was peeled in a part of the samples.

COMPARATIVE EXAMPLE 5

A medical bag was produced in a similar manner to that of Example 1, except that the surface temperature of the upper mold was changed to 140° C., the surface temperature of the lower mold was changed to 115° C., L1/L2 was changed to 5.0, and the conditions for the sterilization were changed to 115° C. and 15 minutes in Example 1.

In the results of the test of Comparative Example 5, all of the persons were able to peel the partition part. Furthermore, the average value of the internal pressures when the partition part was peeled was 11.0 kPa.

However, when impact resistance tests were conducted on plural samples of Comparative Example 5, the partition part was peeled in a part of the samples.

COMPARATIVE EXAMPLE 6

A medical bag was produced in a similar manner to that of Example 1, except that the surface temperature of the upper mold was changed to 140° C., the surface temperature of the lower mold was changed to 115° C., the liquid amount ratio was changed to 1:5.0, and the conditions for the sterilization were changed to 126° C. and 48 minutes in Example 1.

In the results of the test of Comparative Example 6, the partition part could not be peeled.

The medical bag of the present invention has been explained above based on the illustrated exemplary embodiments. However, the present invention is not limited to these exemplary embodiments, and each part can be replaced with a part having an optional constitution capable of exerting a similar function. Furthermore, optional constitutional matters may also be added.

The medical bag according to certain embodiments described above includes a bag main body constituted by a flexible sheet material having an interior portion partitioned via a partition part into a first space and a second space being smaller than the first space, a first liquid housed in the first space, and a second liquid housed in the second space, said medical bag has been obtained by sterilizing at 118 to 125° C. for 20 to 45 minutes, wherein when the volume of the first liquid is set as L1 and the volume of the second liquid is set as L2, L1/L2 is 2.0 to 6.0, and the partition part has a breaking strength of 5 to 25 kPa.

According to certain embodiments, involuntary peeling at the partition part can be inhibited even in sterilization at a relatively high temperature, and the partition part can be easily peeled in use. In this way, even a weak-handed person such as an aged person or a woman can use the medical bag by peeling the partition part easily and surely.

REFERENCE NUMERAL LIST

1 medical bag
10 medical bag individually-packaged body
2 bag main body
21 sheet material
22, 23 sealed part
241, 242, 243 pore
3 first space
30 first liquid
4 second space
40 second liquid
5 partition part
6 injection port
61 injection port main body
62 outer cylinder
65 tube
7 packaging material
71 first sheet material
72 second sheet material
73 space
75 sealed part
76 peel tab
8 mold
81 upper mold
82 lower mold

The invention claimed is:
1. A medical bag comprising:
   a bag main body comprising a flexible sheet material having an interior portion partitioned via a partition part into a first space and a second space that is smaller than the first space;
   a first liquid housed in the first space; and
   a second liquid housed in the second space;
   wherein when a volume of the first liquid is set as L1 and a volume of the second liquid is set as L2, L1/L2 is 2.0 to 6.0;
   wherein the partition part has a breaking strength in a range of 5 to 25 kPa; and wherein the partition part is a part formed by sandwiching and melt-bonding the sheet material between an upper mold disposed on an upper side of the sheet material in a vertical direction and having a surface temperature of 130 to 145° C., and a lower mold disposed on a lower side of the sheet material in the vertical direction and having a surface temperature that is 20 to 30° C. lower than the surface temperature of the upper mold.

2. The medical bag according to claim 1, wherein a liquid formed by mixing the first liquid and the second liquid is a peritoneal dialysate.

3. The medical bag according to claim 1, wherein the first liquid has a pH of 4.0 to 6.0.

4. The medical bag according to claim 1, wherein the first liquid comprises icodextrin.

5. The medical bag according to claim 1, wherein the second liquid is formulated to adjust a pH of the liquid formed by mixing the first liquid and the second liquid to 6.0 to 7.5.

6. The medical bag according to claim 1, wherein the second liquid is a buffer.

7. A method comprising:
providing a flexible sheet material;
forming a medical bag from the flexible sheet, which comprises a step of forming an interior portion partitioned via a partition part into a first space and a second space that is smaller than the first space,
wherein the partition part is formed by sandwiching and melt-bonding the sheet material between an upper mold disposed on an upper side of the sheet material in a vertical direction and having a surface temperature of 130 to 145° C., and a lower mold disposed on a lower side of the sheet material in the vertical direction and having a surface temperature that is 20 to 30° C. lower than the surface temperature of the upper mold, wherein the partition part is formed to have a breaking strength in a range of 5 to 25 kPa.

8. The method of claim 7, further comprising:
supplying a first liquid to the first space; and
supplying a second liquid to the second space.

9. The method of claim 8, wherein, when the volume of the first liquid is set as L1 and the volume of the second liquid is set as L2, L1/L2 is 2.0 to 6.0.

10. The method of claim 8, further comprising sterilizing the medical bag at 118 to 125° C. for 20 to 45 minutes.

11. The medical bag according to claim 1, wherein an edge of the partition part adjacent to the first space extends laterally across the bag main body between the first lateral side and the second lateral side in a wave shape that comprises a plurality of convex portions.

12. The method of claim 7, wherein:
the bag main body has a top side, a bottom side opposite the top side, a first lateral side, and a second lateral side opposite the first lateral side, and wherein the first and second lateral sides are longer than the top and bottom sides, and
an edge of the partition part adjacent to the second space extends laterally across the bag main body between the first lateral side and the second lateral side in a straight line.

13. The method of claim 7, wherein an edge of the partition part adjacent to the first space extends laterally across the bag main body between the first lateral side and the second lateral side in a wave shape that comprises a plurality of convex portions.

14. The medical bag of claim 1, wherein the partition part is a part formed by performing the melt-bonding while the pressure by the mold is 0.2 to 0.5 MPa.

15. The medical bag of claim 14, wherein the partition part is a part formed by sandwiching and melt-bonding the sheet material between the upper mold disposed on the upper side of the sheet material in the vertical direction and having a surface temperature of 135 to 145° C., and the lower mold disposed on the lower side of the sheet material in the vertical direction and having a surface temperature that is 22 to 30° C. lower than the surface temperature of the upper mold.

16. The medical bag of claim 15, wherein the partition part is a part formed by sandwiching and performing the melt-bonding for a melt-bonding time of 2.0 to 5.0 seconds.

17. The method of claim 7, wherein the melt-bonding is performed while the pressure by the mold is 0.2 to 0.5 MPa.

18. The method of claim 17, wherein the partition part is formed by sandwiching and melt-bonding the sheet material between the upper mold disposed on the upper side of the sheet material in the vertical direction and having a surface temperature of 135 to 145° C., and the lower mold disposed on the lower side of the sheet material in the vertical direction and having a surface temperature that is 22 to 30° C. lower than the surface temperature of the upper mold.

19. The method of claim 18, wherein the melt-bonding is performed for a melt-bonding time of 2.0 to 5.0 seconds.

* * * * *